US00PP25487P2

(12) United States Plant Patent
Dummen

(10) Patent No.: US PP25,487 P2
(45) Date of Patent: Apr. 28, 2015

(54) ***CALIBRACHOA* PLANT NAMED 'DUEALKOMIDBU'**

(50) Latin Name: ***Calibrachoa* sp.**
Varietal Denomination: Duealkomidbu

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 66 days.

(21) Appl. No.: 13/987,107

(22) Filed: Jul. 1, 2013

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Kent L Bell
(74) *Attorney, Agent, or Firm* — C. A. Whealy

(57) ABSTRACT

A new and distinct cultivar of *Calibrachoa* plant named 'Duealkomidbu', characterized by its compact, semi-upright to outwardly spreading to trailing and decumbent plant habit; freely branching habit; early and freely flowering habit; large purple violet-colored flowers with dark purple-colored centers; and good garden performance.

1 Drawing Sheet

Botanical designation: *Calibrachoa* sp.
Cultivar denomination: 'DUEALKOMIDBU'.

BACKGROUND OF THE INVENTION

The present invention relates to a new and distinct cultivar of *Calibrachoa* plant, botanically known as *Calibrachoa* sp. and hereinafter referred to by the name 'Duealkomidbu'.

The new *Calibrachoa* plant is a product of a planned breeding program conducted by the Inventor in Rheinberg, Germany. The objective of the breeding program is to create new compact *Calibrachoa* plants with large attractive flowers.

The new *Calibrachoa* plant originated from a cross-pollination made by the Inventor in July, 2010 in Rheinberg, Germany of a proprietary selection of *Calibrachoa* sp. identified as code number A09-1143-002, not patented, as the female, or seed, parent with a proprietary selection of *Calibrachoa* sp. identified as code number A08-4798-003, not patented, as the male, or pollen, parent. The new *Calibrachoa* plant was discovered and selected by the Inventor as a single flowering plant from within the progeny of the stated cross-pollination in a controlled greenhouse environment in Rheinberg, Germany in May, 2012.

Asexual reproduction of the new *Calibrachoa* plant by vegetative terminal cuttings in a controlled greenhouse environment in Rheinberg, Germany since June, 2012 has shown that the unique features of this new *Calibrachoa* plant are stable and reproduced true to type in successive generations.

SUMMARY OF THE INVENTION

Plants of the new *Calibrachoa* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Duealkomidbu'. These characteristics in combination distinguish 'Duealkomidbu' as a new and distinct *Calibrachoa* plant:

1. Compact, semi-upright to outwardly spreading to trailing and decumbent plant habit.
2. Freely branching habit.
3. Early and freely flowering habit.
4. Large purple violet-colored flowers with dark purple-colored centers and venation.
5. Good garden performance.

The new *Calibrachoa* can be compared to plants of the female parent selection. Plants of the new *Calibrachoa* differ primarily from plants of the female parent selection in flower color as plants of the female parent selection have light purple-colored flowers.

The new *Calibrachoa* can be compared to plants of the male parent selection. Plants of the new *Calibrachoa* differ primarily from plants of the male parent selection in plant habit as plants of the new *Calibrachoa* are more compact than plants of the male parent selection. In addition, plants of the new *Calibrachoa* are more freely branching than plants of the male parent selection.

Plants of the new *Calibrachoa* can be compared to plants of *Calibrachoa* sp. 'Mini Famous Compact Dark Blue', not patented. In side-by-side comparisons, plants of the new *Calibrachoa* differed primarily from plants of 'Mini Famous Compact Dark Blue' in the following characteristics:

1. Plants of the new *Calibrachoa* were not as compact as plants of 'Mini Famous Compact Dark Blue'.
2. Plants of the new *Calibrachoa* were more freely branching than plants of 'Mini Famous Compact Dark Blue'.
3. Plants of the new *Calibrachoa* had shorter internodes than plants of 'Mini Famous Compact Dark Blue'.
4. Plants of the new *Calibrachoa* were more freely flowering than plants of 'Mini Famous Compact Dark Blue'.
5. Plants of the new *Calibrachoa* and 'Mini Famous Compact Dark Blue' differed in flower color.

BRIEF DESCRIPTION OF THE PHOTOGRAPH

The accompanying colored photograph illustrates the overall appearance of the new *Calibrachoa* plant showing the colors as true as it is reasonably possible to obtain in colored reproductions of this type. Colors in the photograph may differ slightly from the color values cited in the detailed botanical description which accurately describe the colors of the new *Calibrachoa* plant.

The photograph is a side perspective view of a typical flowering plant of 'Duealkomidbu'.

DETAILED BOTANICAL DESCRIPTION

The aforementioned photograph and following observations, measurements and values describe plants grown during the summer in 10.5-cm containers in a glass-covered greenhouse in Rheinberg, Germany under cultural practices typical of commercial *Calibrachoa* production. During the production of the plants, day and night temperatures averaged 18° C. and light levels averaged 4,500 lux. Rooted young plants were pinched one time three weeks after planting and plants were 13 weeks old when the photograph and description were taken. In the following description, color references are made to The Royal Horticultural Society Colour Chart, 1995 Edition, except where general terms of ordinary dictionary significance are used.

Botanical classification: *Calibrachoa* sp. 'Duealkomidbu'.

Parentage:

- *Female, or seed, parent*.—Proprietary selection of *Calibrachoa* sp. identified as code number A09-1143-002, not patented.
- *Male, or pollen, parent*.—Proprietary selection of *Calibrachoa* sp. identified as code number A08-4798-003, not patented.

Propagation:

- *Type*.—By vegetative cuttings.
- *Time to initiate roots, summer*.—About five days at temperatures of 20° C.
- *Time to initiate roots, winter*.—About seven days at temperatures of 20° C.
- *Time to produce a rooted young plant, summer*.—About three weeks at temperatures of 20° C.
- *Time to produce a rooted young plant, winter*.—About four weeks at temperatures of 20° C.
- *Root description*.—Fine, fibrous; white in color.
- *Rooting habit*.—Freely branching; dense.

Plant description:

- *Plant and growth habit*.—Compact, semi-upright to outwardly spreading to trailing and decumbent plant habit; freely branching habit with about 155 to 160 lateral branches developing per plant; pinching enhances branching; vigorous growth habit; moderate growth rate.
- *Plant height*.—About 21 cm.
- *Plant diameter*.—About 65.5 cm.

Lateral branch description:

- *Length*.—About 17 cm.
- *Diameter*.—About 1.9 mm.
- *Internode length*.—About 1.4 cm.
- *Strength*.—Strong.
- *Aspect*.—Initially upright to outwardly spreading to trailing and decumbent.
- *Texture*.—Pubescent.
- *Color*.—Close to 144B.

Leaf description:

- *Arrangement*.—Alternate, simple.
- *Length*.—About 3 cm.
- *Width*.—About 1.5 cm.
- *Shape*.—Oblanceolate.
- *Apex*.—Rounded.
- *Base*.—Cuneate.
- *Margin*.—Entire.
- *Texture, upper and lower surfaces*.—Pubescent.
- *Venation pattern*.—Pinnate; arcuate.
- *Color*.—Developing leaves, upper and lower surfaces: Close to 137C. Fully expanded leaves, upper surface: Close to 137A; venation, close to 137B. Fully expanded leaves, lower surface: Close to 137C; venation, close to 144B.
- *Petioles*.—Length: About 5.6 mm. Diameter: About 2 mm. Texture, upper and lower surfaces: Pubescent. Color, upper and lower surfaces: Close to 144B.

Flower description:

- *Flower arrangement and habit*.—Single salverform flowers arising from leaf axils; freely flowering habit with usually about 480 to 520 flowers developing per plant; flowers face upright or outwardly.
- *Fragrance*.—None detected.
- *Natural flowering season*.—Early flowering habit, plants of the new *Calibrachoa* initiate and develop flowers about four to five weeks after planting; plants flower continuously from the spring throughout the summer in Germany.
- *Flower longevity*.—Individual flowers last about seven to ten days on the plant; flowers not persistent.
- *Flower diameter*.—About 3.9 cm.
- *Flower length* (*height*).—About 2.6 cm.
- *Flower throat diameter*.—About 8.8 mm.
- *Flower tube length*.—About 1.8 cm.
- *Flower tube diameter, base*.—About 1.5 mm to 2 mm.
- *Flower buds*.—Length: About 2.1 cm. Diameter: About 4.4 mm. Shape: Elongated oblong. Color: Close to 79A and 145B.
- *Corolla*.—Arrangement: Five petals fused at the base and opening into a flared trumpet. Petal length from throat: About 1.5 cm. Petal lobe width: About 1.8 cm. Petal shape: Roughly spatulate. Petal apex: Mostly rounded. Petal margin: Entire. Petal texture, upper and lower surfaces: Smooth, glabrous. Throat texture: Smooth, glabrous. Tube texture: Smooth, glabrous. Color: Petal, when opening, upper surface: Close to 83A. Petal, when opening, lower surface: Close to 79C. Petal, fully opened, upper surface: Close to 81A; venation and towards the throat, close to 79A; color does not change with development. Petal, fully opened, lower surface: Close to 77A; venation, close to 79A. Throat: Close to 153A; venation, close to 79A. Tube: Close to 145B; venation, close to 79A.
- *Calyx*.—Arrangement: Star-shaped calyx with five sepals; sepals fused at the base. Sepal length: About 1.5 cm. Sepal width: About 4.3 mm. Sepal shape: Lanceolate. Sepal apex: Acute. Sepal margin: Entire. Sepal texture, upper and lower surfaces: Pubescent. Color, upper and lower surfaces: Close to 137B.
- *Peduncles*.—Length: About 1.9 cm. Diameter: About 1 mm. Angle: About 45° from stem axis. Strength: Moderately strong. Texture: Pubescent. Color: Close to 144A.

*Reproductive organs*.—Stamens: Quantity: Six per flower. Filament length: About 8.6 mm. Filament color: Close to 145B. Anther shape: Ellipsoidal. Anther length: About 0.5 mm to 1 mm. Anther color: Close to 3C. Pollen amount: Scarce. Pollen color: Close to 15C. Pistils: Quantity: One per flower. Pistil length: About 9.6 mm. Style length: About 7 mm. Style color: Close to 144B. Stigma shape: Ellipsoidal. Stigma color: Close to 144A. Ovary color: Close to 144C. Seeds and fruits: Seed and fruit development have not been observed on plants of the new *Calibrachoa*.

Garden performance: Plants of the new *Calibrachoa* have been observed to have good garden performance and tolerate wind, rain and temperatures ranging from about 5° C. to about 40° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'Duealkomidbu' as illustrated and described.

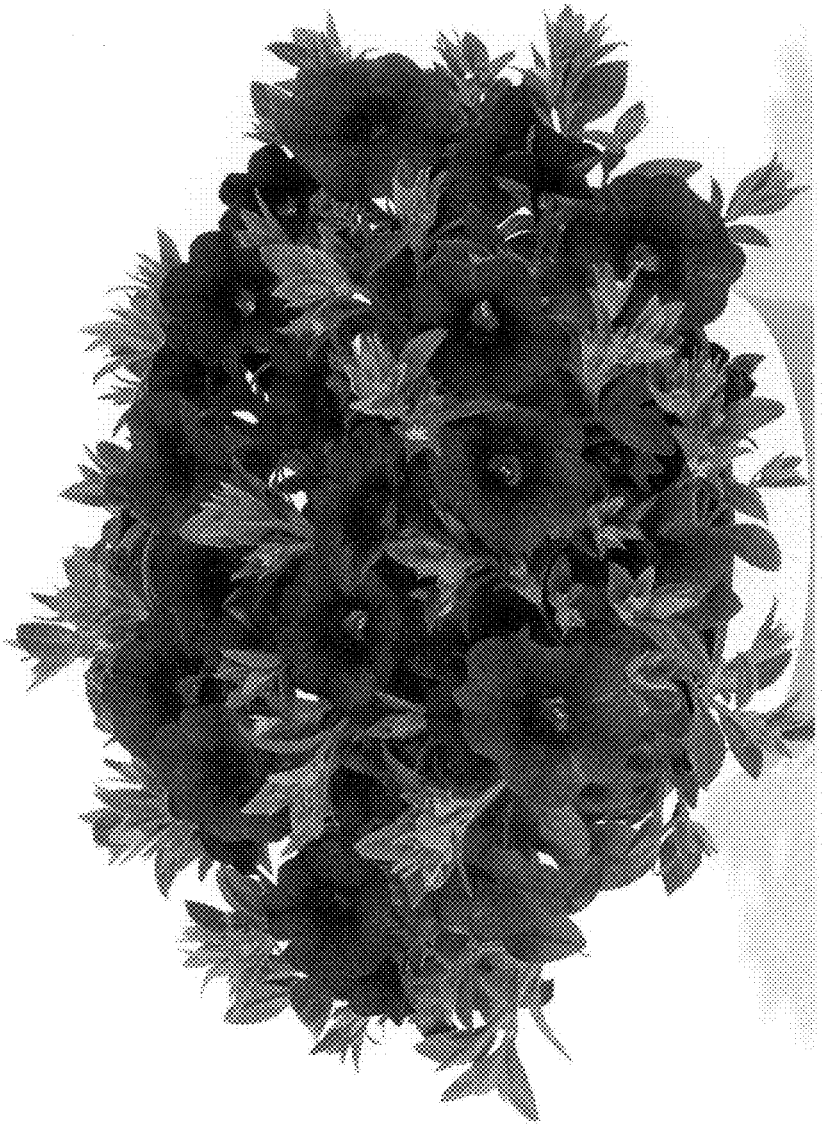

* * * * *